United States Patent
Wakita

(10) Patent No.: US 9,561,171 B2
(45) Date of Patent: Feb. 7, 2017

(54) LOW PLATINUM CONTENT HYDROSILYLATION REACTION-CROSSLINKED SILICONE RUBBER POWDER

(71) Applicant: DOW CORNING TORAY CO., LTD., Tokyo (JP)

(72) Inventor: Mari Wakita, Chiba (JP)

(73) Assignee: Dow Corning Toray Co., Ltd., Tokyo (JP)

( * ) Notice: Subject to any disclaimer, the term of this patent is extended or adjusted under 35 U.S.C. 154(b) by 0 days.

(21) Appl. No.: 14/654,625

(22) PCT Filed: Dec. 13, 2013

(86) PCT No.: PCT/JP2013/084178
§ 371 (c)(1),
(2) Date: Jun. 22, 2015

(87) PCT Pub. No.: WO2014/098205
PCT Pub. Date: Jun. 26, 2014

(65) Prior Publication Data
US 2015/0306019 A1    Oct. 29, 2015

(30) Foreign Application Priority Data
Dec. 22, 2012 (JP) .................. 2012-280345

(51) Int. Cl.
| | | |
|---|---|---|
| *A61K 8/895* | (2006.01) | |
| *A61K 8/02* | (2006.01) | |
| *C08G 77/34* | (2006.01) | |
| *C08G 77/38* | (2006.01) | |
| *C08G 77/20* | (2006.01) | |
| *C08G 77/12* | (2006.01) | |

(52) U.S. Cl.
CPC .............. *A61K 8/895* (2013.01); *A61K 8/0245* (2013.01); *C08G 77/34* (2013.01); *C08G 77/38* (2013.01); *A61K 2800/80* (2013.01); *C08G 77/12* (2013.01); *C08G 77/20* (2013.01)

(58) Field of Classification Search
CPC ........... C08L 83/04; C08L 71/02; C08L 83/00; C08K 5/56; A61K 2800/80; A61K 8/0245; A61K 8/895; C08G 77/12; C08G 77/20; C08G 77/34; C08G 77/38
See application file for complete search history.

(56) References Cited

U.S. PATENT DOCUMENTS

| | | | |
|---|---|---|---|
| 4,594,134 A | 6/1986 | Hanada et al. | |
| 4,742,142 A | 5/1988 | Shimizu et al. | |
| 4,743,670 A | 5/1988 | Yoshida et al. | |
| 6,280,749 B1 * | 8/2001 | Omura .................. | A61K 8/897 423/324 |
| 2008/0210129 A1 | 9/2008 | Nienstedt et al. | |
| 2010/0112023 A1 | 5/2010 | Inokuchi et al. | |
| 2010/0112074 A1 | 5/2010 | Inokuchi et al. | |

FOREIGN PATENT DOCUMENTS

| | | |
|---|---|---|
| EP | 0304946 A2 | 3/1989 |
| EP | 0972787 A1 | 1/2000 |
| JP | S59-068333 A | 4/1984 |
| JP | S62-243621 A | 10/1987 |
| JP | S63-077942 A | 4/1988 |
| JP | S64-070558 A | 3/1989 |
| JP | 2010-132877 A | 6/2010 |
| JP | 2010-132878 A | 6/2010 |
| WO | WO03/080788 A2 | 10/2003 |

OTHER PUBLICATIONS

PCT/JP2013/084178 International Search Report dated Jun. 23, 2014, 3 pages.

* cited by examiner

*Primary Examiner* — Aradhana Sasan
(74) *Attorney, Agent, or Firm* — Warner Norcross & Judd LLP

(57) ABSTRACT

A method to produce a hydrosilylation reaction-crosslinkable silicone rubber powder includes washing the hydrosilylation reaction-crosslinkable silicone rubber powder using an aqueous solution. The aqueous solution can be heated to a temperature of 30° C. to 99° C. The aqueous solution contains at least one type of surfactant. The hydrosilylation reaction-crosslinkable silicone rubber powder produced via the method has a platinum metal content ≤3.5 ppm by mass. The hydrosilylation reaction-crosslinkable silicone rubber powder can be used for various applications, including use in a cosmetic composition, which can also include a cosmetic raw material.

20 Claims, No Drawings

LOW PLATINUM CONTENT HYDROSILYLATION REACTION-CROSSLINKED SILICONE RUBBER POWDER

CROSS-REFERENCE TO RELATED APPLICATIONS

This application is the National Stage of International Patent Application No. PCT/JP2013/084178, filed on Dec. 13, 2013, which claims priority to and all the advantages of Japanese Patent Application No. 2012-280345, filed on Dec. 22, 2012, the content of which is hereby incorporated by reference.

BRIEF SUMMARY OF THE INVENTION

Disclosed is a low platinum content hydrosilylation reaction-crosslinkable silicone rubber powder that has a platinum metal content ≤3.5 ppm by mass relative to the silicone rubber powder mass. Also disclosed is a cosmetic raw material- and cosmetic composition-related applications of the hydrosilylation reaction-crosslinkable silicone rubber powder. Also disclosed is a process to produce the silicone rubber powder, post treatment processing of a silicone rubber powder, with the object of lowering the platinum metal content of the hydrosilylation reaction-crosslinkable silicone rubber powder.

Silicone rubber powders can be used by blending in cosmetic compositions for improving the feel of use of the cosmetic compositions. Silicone rubber powders are widely used as raw materials for cosmetic compositions, external use preparations, and quasi-drugs, whether the system is oily or aqueous. In particular, hydrosilylation reaction-crosslinkable silicone rubber powders using a hydrosilylation reaction catalyst including a platinum type metal are widely used as silicone rubber powders due to rapid curing, easy control of the reaction, and the ability to select various types of curing conditions.

Production methods for a hydrosilylation reaction-crosslinkable silicone rubber powder are exemplified by a method of curing a hydrosilylation-reaction crosslinkable liquid silicone rubber composition by curing while the hydrosilylation-reaction crosslinkable liquid silicone rubber composition is sprayed in hot air (see Japanese Unexamined Patent. Application Publication No. S59-068333A); and methods that cure a liquid silicone rubber composition while the liquid silicone rubber composition is dispersed in water using a surfactant, and then remove the water (Japanese Unexamined Patent Application Publication No. S62-243621A, Japanese Unexamined Patent Application Publication No. S63-077942A, and Japanese Unexamined Patent Application Publication No. S64-070558A). Here, the method of curing a liquid silicone rubber composition while dispersed in water is typical due to the ability to prepare uniform spherical silicone rubber powder with good efficiency.

However, in the known production methods, the platinum hydrosilylation reaction catalyst is incorporated in the surface or interior of the silicone rubber powder due to crosslinking, and thus remains in the silicone rubber powder product. The platinum metal in the silicone rubber powder reacts with other cosmetic raw materials, causes changes of properties or odorization, and may cause discoloration by forming platinum black or metal complexes. It is thus desirable to lower the platinum metal content in the silicone rubber powder as much as possible, and more specifically to a level ≤3.5 ppm by mass of the total silicone rubber powder.

However, the platinum metal included in the hydrosilylation reaction catalyst is incorporated in the crosslinked structure of the silicone rubber, and it is not possible to remove the platinum metal by a normal washing process targeting the removal of a foreign object. Additionally known treatment processes using organic solvents have had a problem of the inability to sufficiently reduce the platinum metal content in the silicone rubber powder. Furthermore, when utilizing the method of treatment using an organic solvent, problems occur such as a great increase of environmental burden, remaining of strongly irritating organic solvent in the obtained silicone rubber powder, odorization due to the solvent, or the like. Thus, the method of treatment using an organic solvent sometimes may not be used with the object of obtaining a cosmetic composition composed of a low platinum content silicone rubber powder.

On the other hand, the aforementioned known references, such as Japanese Unexamined Patent Application Publication No. S64-070558A and Japanese Unexamined Patent Application Publication No. 2010-132878A, mention that a platinum metal content of about 1 to 100 ppm may be used for the curing reaction. However, the time of production is excessively prolonged when using <5 ppm by mass for the hydrosilylation reaction, and generally a platinum metal content of about 5 to 20 ppm by mass is adopted for economics in an actual silicone rubber powder industrial production process (see the practical examples in the various references). If reaction conditions were to be adopted at an industrial scale resulting in a platinum content below this level, due to the increase in cycle time, production would become difficult from the standpoint of economics.

For this reason, not only is there no specific disclosure in the aforementioned known references of a hydrosilylation reaction-crosslinkable silicone rubber powder having a platinum metal content ≤3.5 ppm by mass, according to disclosure of the aforementioned known references, there has been a problem in that a low platinum content hydrosilylation reaction-crosslinkable silicone rubber powder can not be obtained in an actual industrial production process.

Furthermore, these known references disclose manufacturing methods for silicone rubber that use a platinum metal-containing hydrosilylation reaction catalyst for curing a liquid silicone rubber composition while the silicone rubber composition is dispersed in water using a surfactant, and thereafter removing the water. However, there is neither mention nor suggestion of washing the obtained silicone rubber powder using an aqueous solution of a nonionic type surfactant.

Moreover, in Japanese Unexamined Patent Application Publication No. 2010-132877A and Japanese Unexamined Patent Application Publication No. 2010-132878A, when adding platinum metal-type catalyst to an emulsion of the liquid silicone rubber composition prior to curing, if the dispersibility of the platinum metal-type catalyst in water is poor, there is a mention of adding the platinum metal-type catalyst as an emulsion in a state produced by dissolving in a surfactant (e.g. paragraph 0045 of Japanese Unexamined Patent Application Publication No. 2010-132878A). However, there is neither mention nor suggestions of washing the obtained silicone rubber powder using an aqueous solution of a nonionic type surfactant.

DETAILED DESCRIPTION OF THE INVENTION

An object of the present invention is to provide a low platinum content hydrosilylation reaction-crosslinkable silicone rubber powder capable of being produced using a simple process suitable for use in industrial production, and that does not adversely affect other cosmetic raw materials and does not cause problems of odorization and discoloration. Similarly, objects of the present invention are to provide an cosmetic application and a suitable production method of the low platinum content hydrosilylation reaction-crosslinkable silicone rubber powder.

The inventors of the present invention discovered the ability to extremely effectively lower platinum metal content in hydrosilylation reaction-crosslinkable silicone rubber powder by washing crosslinkable silicone rubber powder obtained by hydrosilylation reaction using an aqueous solution of at least one type of surfactant, and more alternatively an aqueous solution including polyoxyethylene alkyl ether or sodium diethylhexyl sulfosuccinate, heated to a temperature of 30° C. to 99° C.

The hydrosilylation reaction-crosslinkable silicone rubber powder of the present invention has a platinum metal content ≤3.5 ppm by mass. In the range of cycle time and at the scale capable of use for industrial production, unwashed silicone rubber powder obtained by hydrosilylation reaction contains at least 5.0 ppm by mass of platinum. However, the present invention is able to realize a reduction in platinum metal content by washing the obtained silicone rubber powder using an aqueous solution of at least one type of surfactant described below.

Although platinum metal content in the hydrosilylation reaction-crosslinkable silicone rubber powder of the present invention is in the range of 0.0 to 3.5 ppm by mass, using a cycle time and scale capable of use for industrial production, the platinum metal content in the hydrosilylation reaction-crosslinkable silicone rubber powder is typically in the range of 1.5 to 3.0 ppm by mass, alternatively in the range of 1.6 to 2.9 ppm by mass. Furthermore, if washing by the aqueous solution of surfactant is repeated over a long time interval, it is possible to lower the platinum metal content to from 0.0 to 0.5 ppm by mass. However, in practice, when the platinum metal content is ≤3.5 ppm by mass (alternatively ≤3.0 ppm by mass, alternatively ≤2.6 ppm by mass), the object of the invention may be attained in that there is no adverse effect of the platinum in the silicone rubber powder on other cosmetic raw materials, and there is no occurrence of odorization and discoloration.

Although no particular limitation is placed on the hydrosilylation reaction-crosslinkable silicone rubber powder of the present invention, an average particle diameter thereof is typically from 0.1 μm to 10 mm, alternatively is from 0.1 μm to 1 mm, alternatively is from 0.1 μm to 500 μm. A particle shape of this silicone rubber powder is exemplified by non-spherical, regular spherical, ellipsoidal, and irregularly shaped. Spherical and regular spherical shapes are typical.

Moreover, from the standpoint of use as a cosmetic raw material, the silicone rubber powder typically is non-tacky, and when the hydrosilylation reaction-crosslinkable silicone rubber composition is cured to form a sheet-like cured product, the rubber hardness measured by a JIS A hardness meter as specified in JIS K 6301 is alternatively in the range of 5 to 99, and further alternatively is in the range of 20 to 70. In particular, when rubber hardness is within the aforementioned range, agglomeration of the obtained silicone rubber powder is sufficiently suppressed, and the obtained silicone rubber powder readily has good fluidity and dispersibility, and has excellent clean, smooth, and soft feel.

No particular limitation is placed on the method of preparing the unwashed silicone rubber powder. The unwashed silicone rubber powder may be produced by methods exemplified by: a method of obtaining a silicone cured product by curing a hydrosilylation reaction-crosslinkable silicone rubber composition comprising (A) an organopolysiloxane having at least two alkenyl groups in a molecule, (B) an organohydrogenpolysiloxane having at least two silicon-bonded hydrogen atoms in a molecule, and (C) a platinum-based catalyst, and using a pulverizing apparatus such as a grinder or the like to pulverize the silicone cured product; a method of curing the hydrosilylation reaction-crosslinkable silicone rubber composition by spraying the hydrosilylation reaction-crosslinkable silicone rubber composition in hot air using a spraying apparatus such as a spray dryer or the like; and a method of dispersing the hydrosilylation reaction-crosslinkable silicone rubber composition in a surfactant aqueous solution and curing the hydrosilylation reaction-crosslinkable silicone rubber composition. Due to the ability to form a uniform spherical silicone rubber powder, the typical method cures the hydrosilylation reaction-crosslinkable silicone rubber composition while the hydrosilylation reaction-crosslinkable silicone rubber composition is dispersed in water using a surfactant, and then removes the water.

The platinum-based catalyst (C) is exemplified by platinum fine powder, chloroplatinic acid, an alcohol solution of chloroplatinic acid, a platinum-alkenylsiloxane complex, a platinum-olefin complex, a platinum-carbonyl complex, platinum black, and platinum supported on silica, or the like. The catalyst (C) is alternatively a platinum-alkenylsiloxane complex. From the standpoint of an industrial production process, the utilized amount of the platinum-based catalyst is an amount such that the platinum metal content becomes at least 5.0 ppm by mass, alternatively in the range of 5 to 100 ppm by mass, alternatively in the range of 5 to 20 ppm by mass, relative to the mass of the cured product resulting from crosslinking of the components (A) and (B). When the amount of the platinum metal in the (C) is less than the lower limit, it becomes difficult to realize production from the standpoint of economics due to the increase in cycle time. On the other hand, when the amount of the platinum metal exceeds the upper limit, a large amount of platinum metal may remain in the silicone rubber powder, and this would impede the object of the present invention, i.e. to provide a low platinum content hydrosilylation reaction-crosslinkable silicone rubber powder.

The alkenyl group of the organopolysiloxane (A) having at least two alkenyl groups in a molecule is exemplified by vinyl groups, allyl groups, butenyl groups, pentenyl groups, and hexenyl groups; and vinyl groups and hexenyl groups are preferred. The non-alkenyl groups bonded to the silicon atom are exemplified by substituted or unsubstituted monovalent hydrocarbon groups as exemplified by alkyl groups such as methyl groups, ethyl groups, propyl groups, butyl groups, and the like; cycloalkyl groups such as cyclopentyl groups, cyclohexyl groups, and the like; aryl groups such as phenyl groups, tolyl groups, xylyl groups and the like; aralkyl groups such as benzyl groups, phenethyl groups, 3-phenylpropyl groups, and the like; halogenated alkyl groups such as 3-chloropropyl groups, 3,3,3-trifluoropropyl groups, and the like; or the like. A molecular structure of the organopolysiloxane (A) having at least two alkenyl groups in a molecule is exemplified by straight, cyclic, net-like, and partially branched straight structures. The straight and partially branched straight structures are particularly preferred. A viscosity of the organopolysiloxane (A) having at least two alkenyl groups in a molecule is alternatively a viscosity capable of allowing dispersion of the hydrosilylation reaction-crosslinkable silicone composition in water. Specifically, the viscosity of the organopolysiloxane (A) having at least two alkenyl groups in a molecule at 25° C. is alternatively in the range of 20 to 100,000 mPa·s, and further alternatively is in the range of 20 to 10,000 mPa·s.

Furthermore, from the standpoint of improvement of oil absorptivity of the obtained hydrosilylation reaction-crosslinkable silicone rubber powder, the organopolysiloxane of the component (A) alternatively has a dimethylsiloxane unit (represented by the formula: —$(CH_3)_2SiO$—) content that is at least 90 mol % of the total siloxane units other than the molecular terminal siloxane units. In the same manner, from the standpoint of improving oil absorptivity of the obtained hydrosilylation reaction-crosslinkable silicone rubber powder, cyclic or chain organopolysiloxanes of a low degree of polymerization (i.e. degree of polymerization=3 to 20) are alternatively removed in advance by stripping or the like.

The non-hydrogen groups bonded to the silicon atoms in the organohydrogenpolysiloxane (B) having at least two silicon-bonded hydrogen atoms in a molecule are exemplified by the substituted or unsubstituted monovalent hydrocarbon groups cited above. The organohydrogenpolysiloxane (B) having at least two silicon-bonded hydrogen atoms in a molecule may have a straight, cyclic, net-like, or a partially branched straight chain molecular structure. Moreover, the viscosity is alternatively a viscosity such that the hydrosilylation reaction-crosslinkable silicone composition may be dispersed in water. Specifically, the viscosity at 25° C. is alternatively in the range of 1 to 10,000 mP·s.

No particular limitation is placed on the contents of components (A) and (B) as long as these contents allow curing of the composition by addition reaction. However, these contents alternatively result in the number of alkenyl groups in the component (A) relative to a single silicon-bonded hydrogen atom in the component (B) becoming 0.5 to 4.0, and further alternatively becoming 0.5 to 2.0. Moreover, the content of the component (B) is alternatively in the range of 0.3 to 500 parts by mass relative to 100 parts by mass of the organopolysiloxane having the alkenyl groups.

By emulsification and curing of the hydrosilylation reaction-crosslinkable silicone rubber composition in the surfactant aqueous solution, it is possible to readily adjust the particle diameter of the hydrosilylation reaction-crosslinkable silicone rubber powder. This surfactant is exemplified by nonionic type surfactants, anion type surfactants, cation type surfactants, and betaine type surfactants. The particle diameter of the obtained cured silicone particles will differ according to the type and content of the surfactant. In order to prepare cured silicone particles of a small particle diameter, the added amount of this surfactant per 100 parts by mass of the crosslinkable silicone rubber composition is alternatively in the range of 0.5 to 50 parts by mass. Conversely, in order to prepare cured silicone rubber powder of a large particle diameter, the added amount of this surfactant per 100 parts by mass of the crosslinkable silicone rubber composition is typically in the range of 0.1 to 10 parts by mass. Furthermore, the added amount of water as a dispersing medium per 100 parts by mass of the crosslinkable silicone rubber composition is in the range of 20 to 1,500 parts by mass, alternatively 50 to 1,000 parts by mass. These surfactants may be blended without modification in the cosmetic composition, and the silicone rubber powder of the present invention may be used as a cosmetic raw material.

Emulsification equipment is alternatively used for uniform dispersion of the hydrosilylation reaction-crosslinkable silicone rubber composition in water. This emulsification equipment is exemplified by a homomixer, a paddle mixer, a Henschel mixer, a homo-disper, a colloid mill, a propeller stirrer, a homogenizer, an in-line continuous emulsifier, an ultrasonic emulsifier, or a vacuum kneader.

Thereafter, the aqueous type dispersion of the hydrosilylation reaction-crosslinkable silicone rubber composition prepared by the aforementioned method may be heated or left at room temperature to allow curing of the crosslinkable silicone rubber composition in this aqueous dispersion, and an aqueous dispersion of silicone rubber powder may be prepared. If the aqueous dispersion of the crosslinkable silicone rubber composition is heated, the heating temperature is typically ≤100° C., alternatively is from 10 to 95° C. Moreover, the method for heating the aqueous dispersion of the crosslinkable silicone rubber composition is exemplified by a method of directly heating this aqueous dispersion, and a method of adding this aqueous dispersion to hot water. Thereafter, the hydrosilylation reaction-crosslinkable silicone rubber powder may be prepared by removal of water from aqueous dispersion of the silicone rubber powder. Methods for removal of water from the aqueous dispersion of the hydrosilylation reaction-crosslinkable silicone rubber powder are exemplified by drying methods using a vacuum dryer, circulating hot air oven, or spray dryer.

Even if a nonionic type surfactant is used as the surfactant, the aforementioned moisture removal process of the aforementioned method differs from a washing process in that the platinum metal content in the silicone rubber powder is not reduced. Although part of the platinum-containing hydrosilylation reaction catalyst that was not incorporated in the crosslinked system of the silicone rubber powder is thought to be present in the aqueous phase in the form of an aqueous dispersion, at the time of removal of water by drying, it is hypothesized that the platinum-containing hydrosilylation reaction catalyst is incorporated on the surface or in the interior of the silicone rubber powder.

The platinum metal content in the silicone rubber powder is not reduced by the method of using a pulverizer such as a grinder or the like for pulverization of the silicone rubber cured product obtained by curing the hydrosilylation reaction-crosslinkable silicone rubber composition. The platinum metal content in the silicone rubber powder is also not reduced by the method of spraying and curing the hydrosilylation reaction-crosslinkable silicone rubber composition in hot air using a spraying apparatus such as a spray dryer or the like.

The present invention is characterized by reducing the platinum content of the silicone rubber powder obtained by the aforementioned method by washing the silicone rubber powder using an aqueous solution of at least one type of surfactant.

No particular limitation is placed on the washing process using an aqueous solution of a nonionic type surfactant, as long as this process includes a step of contacting the aqueous solution of surfactant with high platinum content hydrosilylation reaction-crosslinkable silicone rubber powder, and, thereafter, a step of separation (i.e. drainage or the like) of the aqueous solution of surfactant from the hydrosilylation reaction-crosslinkable silicone rubber powder having lowered platinum content. As long as the washing process is performed at least once, it is also possible to perform the washing process multiple times to reach a desired platinum metal content. For example, the aqueous solution of surfactant and the high platinum content hydrosilylation reaction-crosslinkable silicone rubber powder are placed in a batch type vessel equipped with an agitator device or the like, and the silicone rubber powder is water washed by immersing in the aqueous phase or by stirring in the aqueous phase for a desired time interval. Thereafter, the hydrosilylation reaction-crosslinkable silicone rubber powder having lowered platinum content may be separated out by filtration. In the same manner, the high platinum content hydrosilylation reaction-crosslinkable silicone rubber powder may be placed on a filtration device such as a mesh or the like, washing may be performed by circulating the aqueous solution of surfactant through the silicone rubber powder layer once or multiple times, and the hydrosilylation reaction-crosslinkable silicone rubber powder having lowered platinum content may be separated out.

The aforementioned washing process using the aqueous solution of surfactant is able to be performed as a process independent from the production of the high platinum content hydrosilylation reaction-crosslinkable silicone rubber powder, and the washing process using the aqueous solution of surfactant is alternatively performed as a process independent from the production of the high platinum content hydrosilylation reaction-crosslinkable silicone rubber powder. The method of producing the hydrosilylation reaction-crosslinkable silicone rubber powder according to the invention of the present application is advantageous due to the ability to be performed quite simply using known equipment as a method for reducing platinum metal content of any silicone rubber powder. For example, a high platinum content hydrosilylation reaction-crosslinkable silicone rubber powder produced by a third party may be used to make a reduced platinum metal content silicone rubber powder by use of an aqueous solution of surfactant for washing such high platinum content silicone rubber powder, using desired equipment or apparatus of the party who has purchased the high platinum content silicone rubber powder. A practical benefit is that even a party who does not self-produce the hydrosilylation reaction-crosslinkable silicone rubber powder may be able to use commercial high platinum content hydrosilylation reaction-crosslinkable silicone rubber powder to easily produce a low platinum content silicone rubber powder.

The washing process using the aqueous solution of surfactant is typically performed using an aqueous solution containing surfactant heated to a temperature of 30° C. to 99° C. By the use of a heated aqueous solution, it is possible to increase the concentration of surfactant, it is possible to prevent precipitation of the surfactant on the silicone rubber powder, and it is possible to efficiently lower the platinum metal content in the hydrosilylation reaction-crosslinkable silicone rubber powder. In particular, the washing alternatively uses an aqueous solution heated to from 35° C. to 99° C., alternatively 40° C. to 99° C., alternatively 40° C. to 60° C. Furthermore, if the high platinum content hydrosilylation reaction-crosslinkable silicone rubber powder and aqueous solution of surfactant are placed in a batch type vessel equipped with a stirring device or the like, and if the silicone rubber powder is washed by stirring or immersing in the aqueous phase for a desired time interval, the vessel itself is particularly alternatively provided with a heater or a constant temperature device so that washings may be performed successively in the aforementioned temperature range.

Moreover, although no particular limitation is placed on the step of separation to remove the aqueous solution by drainage or the like after the washing, this is alternatively performed by drainage of the aqueous solution after washing by subjecting the silicone rubber powder to centrifugal separation or the like.

No particular limitation is placed on the concentration of the surfactant in the aqueous solution of the surfactant as long as the platinum metal content can be reduced. However, this concentration is typically in the range of 0.1 to 10% by mass, alternatively at least 0.3% by mass, alternatively 0.50 to 5.0% by mass.

The surfactant may be at least one type selected from the group consisting of anionic surfactants, cationic surfactants, nonionic surfactants, and amphoteric surfactants. In particular, the use of a nonionic surfactant or an anionic surfactant is preferred. From the standpoint of efficient reduction in the platinum metal content, the use of an α-sulfofatty acid ester salt such as sodium diethylhexyl sulfosuccinate or the like or a polyoxyalkylene alkyl ether having an HLB value of 7.0 to 16.5 is particularly preferred, although the surfactant is not limited to these examples.

Examples of anionic surfactants include saturated or unsaturated fatty acid salts (e.g. sodium laurate, sodium stearate, sodium oleate, sodium linolenate, and the like); alkylsulfuric acid salts; alkylbenzene sulfonic acids (e.g. hexylbenzenesulfonic acid, octylbenzenesulfonic acid, dodecylbenzenesulfonic acid, and the like) and salts thereof; polyoxyalkylene alkyl ether sulfuric acid salts; polyoxyalkylene alkenyl ether sulfuric acid salts; polyoxyethylene alkylsulfuric ester salts; sulfosuccinic acid alkyl ester salts; polyoxyalkylene sulfosuccinic acid alkyl ester salts; polyoxyalkylene alkylphenyl ether sulfuric acid salts; alkanesulfonic acid salts; octyltrimethylammonium hydroxide; dodecyltrimethylammonium hydroxide; alkyl sulfonates; polyoxyethylene alkylphenyl ether sulfuric acid salts; polyoxyalkylene alkyl ether acetic acid salts; alkyl phosphoric acid salts; polyoxyalkylene alkyl ether phosphoric acid salts; acylglutamic acid salts; α-acylsulfonic acid salts; alkylsulfonic acid salts; alkylallylsulfonic acid salts; α-olefinsulfonic acid salts; alkylnaphthalene sulfonic acid salts; alkanesulfonic acid salts; alkyl or alkenylsulfuric acid salts; alkylamide sulfuric acid salts; alkyl- or alkenyl phosphoric acid salts; alkylamide phosphoric acid salts; alkyloylalkyl taurine salts; N-acylamino acid salts; sulfosuccinic acid salts; alkyl ether carboxylic acid salts; amide ether carboxylic acid salts; α-sulfofatty acid ester salts; alanine derivatives; glycine derivatives; and arginine derivatives. Examples of salts include alkali metal salts such as sodium salts and the like, alkaline earth metal salts such as magnesium salts and the like, alkanolamine salts such as triethanolamine salts and the like, and ammonium salts.

Examples of cationic surfactants include alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, distearyldimethylammonium chloride, dicocoyldimethylammonium chloride, dioctyldimethylammonium chloride, di(POE)oleylmethylammonium (2 EO) chloride, benzalkonium chloride, alkyl benzalkonium chloride, alkyl dimethylbenzalkonium chloride, benzethonium chloride, stearyl dimethylbenzylammonium chloride, lanolin derivative quaternary ammonium salt, diethylaminoethylamide stearate, dimethylaminopropylamide stearate, behenic acid amide propyldimethyl hydroxypropylammonium chloride, stearoyl colaminoformyl methylpyridinium chloride, cetylpyridinium chloride, tall oil alkylbenzyl hydroxyethylimidazolinium chloride, and benzylammonium salt.

Examples of nonionic surfactants include polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hydrogenated) castor oils, polyoxyalkylene alkyl phenols, polyoxyalkylene alkyl phenyl ethers, polyoxyalkylene phenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerol fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycol, diethyleneglycol, polyoxyalkylene-modified silicones, polyglyceryl-modified silicones, glyceryl-modified silicones, sugar-modified silicones, fluorine-based surfactants, polyoxyethylene/polyoxypropylene block polymers, and alkyl polyoxyethylene/polyoxypropylene block polymer ethers. In particular, a polyoxyalkylene-modified silicone, a polyglyceryl-modified silicone, a glyceryl-modified silicone, or a sugar alcohol-modified silicone may be advantageously subjected to alkyl branching, straight-chain silicone branching, siloxane dendrimer branching, or the like simultaneously with a hydrophilic group as necessary.

Examples of amphoteric surfactants include imidazoline-type, amidobetaine-type, alkylbetaine-type, alkylamidobetaine-type, alkylsulfobetaine-type, amidosulfobetaine-type, hydroxysulfobetaine-type, carbobetaine-type, phosphobetaine-type, aminocarboxylic acid-type, and amidoamino acid-type amphoteric surfactants. Specifically, examples include imidazoline-type amphoteric surfactants such as 2-undecyl-N,N,N-(hydroxyethylcarboxymethyl)-2-imidazoline sodium, 2-cocoyl-2-imidazolinium hydroxide-1-carboxyethyloxy disodium salt, and the like; alkylbetaine-type amphoteric surfactants such as lauryl dimethylaminoacetic betaine, myristyl betaine, and the like; amidobetaine-type amphoteric surfactants such as coconut oil fatty acid amidopropyl dimethylamino acetic acid betaine, palm kernel oil fatty acid amidopropyl dimethylamino acetic acid betaine, beef tallow fatty acid amidopropyl dimethylamino acetic acid betaine, hardened beef tallow fatty acid amidopropyl dimethylamino acetic acid betaine, lauric acid amidopropyl dimethylamino acetic acid betaine, myristic acid amidopropyl dimethylamino acetic acid betaine, palmitic acid amidopropyl dimethylamino acetic acid betaine, stearic acid amidopropyl dimethylamino acetic acid betaine, oleic acid amidopropyl dimethylamino acetic acid betaine, and the like; alkylsulfobetaine-type amphoteric surfactants such as coconut oil fatty acid dimethyl sulfopropyl betaine and the like; alkyl hydroxy sulfobetaine-type amphoteric surfactants such as lauryl dimethylaminohydroxy sulfobetaine and the like; phosphobetaine-type amphoteric surfactants such as laurylhydroxy phosphobetaine and the like; and amidoamino acid-type amphoteric surfactants such as sodium N-lauroyl-N'-hydroxyethyl-N'-carboxymethyl ethylenediamine, sodium N-oleoyl-N'-hydroxyethyl-N'-carboxymethyl ethylenediamine, sodium N-cocoyl-N'-hydroxyethyl-N'-carboxymethyl ethylenediamine, potassium N-lauroyl-N'-hydroxyethyl-N'-carboxymethyl ethylenediamine, potassium N-oleoyl-N'-hydroxyethyl-N'-carboxymethyl ethylenediamine, sodium N-lauroyl-N-hydroxyethyl-N'-carboxymethyl ethylenediamine, sodium N-oleoyl-N-hydroxyethyl-N'-carboxymethyl ethylenediamine, sodium N-cocoyl-N-hydroxyethyl-N'-carboxymethyl ethylenediamine, monosodium N-lauroyl-N-hydroxyethyl-N',N'-dicarboxymethyl ethylenediamine, monosodium N-oleoyl-N-hydroxyethyl-N',N'-dicarboxymethyl ethylenediamine, monosodium N-cocoyl-N-hydroxyethyl-N',N'-dicarboxymethyl ethylenediamine, disodium N-lauroyl-N-hydroxyethyl-N',N'-dicarboxymethyl ethylenediamine, disodium N-oleoyl-N-hydroxyethyl-N',N'-dicarboxymethyl ethylenediamine, disodium N-cocoyl-N-hydroxyethyl-N',N'-dicarboxymethyl ethylenediamine, and the like.

Examples of semipolar surfactants include alkylamine oxide-type surfactants, alkylamine oxides, alkylamide amine oxides, alkylhydroxyamine oxides, and the like. Alkyldimethylamine oxides having from 10 to 18 carbon atoms, alkoxyethyl dihydroxyethylamine oxides having from 8 to 18 carbon atoms, and the like are alternatively used. Specific examples thereof include dodecyldimethylamine oxide, dimethyloctylamine oxide, diethyldecylamine oxide, bis-(2-hydroxyethyl)dodecylamine oxide, dipropyltetradecylamine oxide, methylethylhexadecylamine oxide, dodecylamidopropyldimethylamine oxide, cetyldimethylamine oxide, stearyldimethylamine oxide, tallow dimethylamine oxide, dimethyl-2-hydroxyoctadecylamine oxide, lauryldimethylamine oxide, myristyldimethylamine oxide, stearyldimethylamine oxide, isostearyldimethylamine oxide, coconut fatty acid alkyldimethylamine oxide, caprylic amide propyldimethylamine oxide, capric amide propyldimethylamine oxide, lauric amide propyldimethylamine oxide, myristic amide propyldimethylamine oxide, palmitic amide propyldimethylamine oxide, stearic amide propyldimethylamine oxide, isostearic amide propyldimethylamine oxide, oleic amide propyldimethylamine oxide, ricinoleic amide propyldimethylamine oxide, 12-hydroxystearic amide propyldimethylamine oxide, coconut fatty acid amide propyldimethylamine oxide, palm kernel oil fatty acid amide propyldimethylamine oxide, castor oil fatty acid amide propyldimethylamine oxide, lauric amide ethyldimethylamine oxide, myristic amide ethyldimethylamine oxide, coconut fatty acid amide ethyldimethylamine oxide, lauric amide ethyldiethylamine oxide, myristic amide ethyldiethylamine oxide, coconut fatty acid amide ethyldiethylamine oxide, lauric amide ethyldihydroxyethylamine oxide, myristic amide ethyldihydroxyethylamine oxide, and coconut fatty acid amide ethyldihydroxyethylamine oxide.

The low platinum metal content hydrosilylation reaction-crosslinkable silicone rubber powder obtained by the present invention has greatly lowered discoloration. It is relatively easy to obtain low platinum metal content hydrosilylation reaction-crosslinkable silicone rubber powder that has a b* value ≤−0.70 as measured by the L* a* b* color coordinate system specified by JIS Z 8729. Alternatively, the b* value of the low platinum metal content hydrosilylation reaction-crosslinkable silicone rubber powder obtained by the present invention is in the range of −0.70 to −0.90.

The low platinum metal content hydrosilylation reaction-crosslinkable silicone rubber powder obtained by the present invention may be a composite cured silicone powder produced by coating using an inorganic fine powder and a lipophilic oily agent.

The low platinum metal content hydrosilylation reaction-crosslinkable silicone rubber powder obtained by the present invention may be used to make an aqueous suspension by dispersion in water using the surfactant and an aqueous solvent density adjustment agent such as a desired polyhydric alcohol or the like. In the same manner, the low platinum metal content hydrosilylation reaction-crosslinkable silicone rubber powder obtained by the present invention may be used in the form of a cosmetic product premix by forming an aqueous suspension with another cosmetic raw material component such as a pigment or the like.

The low platinum metal content hydrosilylation reaction-crosslinkable silicone rubber powder obtained by the present invention may be used in the form of a lipophilic silicone rubber powder composition formed by dispersion or permeation using at least one type of oily agent. The hydrosilylation reaction-crosslinkable silicone rubber powder has particularly excellent oil absorptivity, and thus the use of the hydrosilylation reaction-crosslinkable silicone rubber powder as a cosmetic raw material is advantageous in that it is possible to effectively suppress oiliness, stickiness, and the sense of an oily film.

Furthermore, the low platinum metal content hydrosilylation reaction-crosslinkable silicone rubber powder obtained by the present invention may be used as a surface treated silicone rubber powder or composite silicone rubber powder by surface treatment using a hydrolyzable silane or a polyorganosilsesquioxane.

The low platinum metal content hydrosilylation reaction-crosslinkable silicone rubber powder of the present invention may be readily produced at an industrial scale, does not adversely affect other cosmetic raw materials, and does not cause the problems of odorization and discoloration. Furthermore, the dispersibility or compounding stability in a cosmetic composition or the like is good, and when the low platinum metal content hydrosilylation reaction-crosslinkable silicone rubber powder of the present invention is compounded in a cosmetic composition or the like, it is possible to realize a sufficient effect from the addition of the silicone rubber powder. Therefore, the low platinum metal content hydrosilylation reaction-crosslinkable silicone rubber powder of the present invention is useful as a cosmetic raw material. In particular, the low platinum metal content hydrosilylation reaction-crosslinkable silicone rubber powder of the present invention has excellent compatibility with the human body and has excellent cosmetic functionality, i.e. moisture, smoothness, or the like. Thus, the low platinum metal content hydrosilylation reaction-crosslinkable silicone rubber powder of the present invention is quite suitable as a silicone raw material for compounding in a cosmetic composition.

Cosmetic Raw Material.

The cosmetic raw material of the present invention includes the low platinum metal content hydrosilylation reaction-crosslinkable silicone rubber powder. As long as the cosmetic raw material of the present invention is used in a range that does not impede the object of the present invention, the form of the cosmetic raw material of the present invention may be the aforementioned composite cured silicone powder, an aqueous type suspension, cosmetic product premix, oily silicone rubber powder composition, surface-treated silicone rubber powder, or composite silicone rubber powder.

By adding and blending this type of cosmetic raw material of the present invention with the following various types of raw materials, a cosmetic composition is obtained that has good compatibility with the skin and is capable of imparting excellent moisture and smoothness.

The various types of raw materials of the skin cosmetic composition include the above described surfactants, pH modifiers, preservatives, fungicidal agents, rust preventatives, or the like, as well as oils and fats such as avocado oil, almond oil, olive oil, cacao butter, sesame oil, wheat germ oil, safflower oil, shea butter, turtle oil, camellia oil, persic oil, castor oil, grape oil, macadamia nut oil, mink oil, egg yolk oil, tallow, palm oil, rose hip oil, hardened oils, and the like; waxes such as orange roughy oil, carnauba wax, candelilla wax, whale wax, jojoba oil, montan wax, beeswax, lanolin, and the like; hydrocarbons such as liquid paraffin, Vaseline, paraffin, ceresin, microcrystalline wax, squalane, and the like; higher fatty acids such as lauric acid, myristic acid, palmitic acid, stearic acid, oleic acid, behenic acid, undecylenic acid, oxystearic acid, linoleic acid, lanolin acid, synthetic fatty acid and the like; alcohols such as ethyl alcohol, isopropyl alcohol, lauryl alcohol, cetyl alcohol, cetostearyl alcohol, stearyl alcohol, oleyl alcohol, behenyl alcohol, lanolin alcohol, hydrogenated lanolin alcohol, hexyl decanol, octyl dodecanol, isostearyl alcohol, and the like; sterols such as cholesterol, dihydrocholesterol, phytosterol, and the like; fatty acid esters such as ethyl linoleate, isopropyl myristate, isopropyl lanolin fatty acid, hexyl laurate, myristyl myristate, cetyl myristate, octyldodecyl myristate, decyl oleate, octyl dodecyl oleate, hexyldecyl dimethyloctanoate, cetyl isooctanoate, cetyl palmitate, glycerin trimyristate, glycerin tri(caprylic-capric acid), propylene glycol dioleate, glycerin triisostearate, glycerin triisooctanoate, cetyl lactate, myristyl lactate, diisostearyl malate, and the like; humectants such as glycerin, propylene glycol, 1,3-butylene glycol, polyethylene glycol, sodium d,l-pyrrolidone carboxylate, sodium lactate, sorbitol, sodium hyaluronate, and the like; pigments such as colored pigments (such as iron oxide and the like), white pigments (such as zinc oxide, titanium oxide, zirconium oxide, and the like), body pigments (such as mica, talc, sericite, and the like), and the like; silicone oils such as dimethyl polysiloxane, methylphenylpolysiloxane, octamethyltetracyclosiloxane, decamethylcyclopentasiloxane, polyether-modified silicone oil, amino-modified silicone oil, and the like; purified water; thickening agents such as carrageenan, alginic acid, gum Arabic, tragacanth, pectin, starch, xanthan gum, polyvinyl alcohol, polyvinyl pyrrolidone, sodium polyacrylate, polyethylene glycol, and the like; film forming agents such as silicone-acrylate copolymers, silicone resins, acrylic polymers, and the like; as well as ultraviolet radiation absorption agents, antibacterial agents, anti-inflammatory agents, antiperspirant agents, perfumes, antioxidants, and spray agents.

If the cosmetic raw material of the present invention is used for a cosmetic composition for hair, adhesion to hair is good due to blending with various types of raw material such as the surfactants, pH modifiers, antiseptics, anti-mildew agents, rust preventatives, or the like as well as film forming agents, antifreeze agents, oily components, emulsifiers, humectants, anti-dandruff agents, antioxidants, chelating agents, ultraviolet radiation absorption agents, perfumes, and coloring agents. By compounding cosmetic raw material of the present invention with such raw materials in a cosmetic composition for hair, it is possible to obtain a cosmetic composition for hair that imparts excellent moisture and smoothness.

Without particular limitation, specific examples of products that may contain the cosmetic raw material of the present invention include lip cosmetic compositions such as lip cream, lipstick, lip gloss, lip rouge, lip liner, and the like; eye makeup cosmetic compositions such as eye shadow, mascara, eye liner, eyebrow pencil, eye color, and the like; skin care cosmetic compositions and cosmetic products used for the skin such as skin cleanser products, antiperspirant products, ultraviolet radiation blocking products, and the like; scalp hair cosmetic products such as scalp cleaning products, hair styling products, hair coloring products, baldness remedy products, hair rinse products, hair conditioning products, hair treatment products, and the like; bathing cosmetic products; and hair growth agents, baldness remedy agents, pain relief agents, bactericides, anti-inflammatory agents, algefacients, and skin aging prevention agents.

The skin use cosmetic products can be used on any site of the entire body including the scalp, face (including lips, eyebrows, and cheeks), fingers, and fingernails. Specific examples thereof include cleansing gels, cleansing creams, cleansing foams, face washing creams, eye makeup removers, face washing foams, liquid soaps (body soaps), hand soaps, gel-like soaps, shaving creams, nail polish removers, acne treatment cosmetic compositions, and similar skin cleansing agent products; skin creams, scalp treatments, skin milks, milk lotions, emulsions, facial packs, body powders, essences, shaving lotions, massage lotions, and similar skin care products; foundations, liquid foundations, oil-based foundations, makeup bases, powders, face powders, cheek coloring, lip creams, lipsticks, lip glosses, eye creams, mascaras, eyebrow pencils, eyelash cosmetic products, and similar makeup products; deodorants and similar anti-perspirants; and sunscreen agents, tanning use medicaments (sun tanning agent), and similar ultraviolet light blocking products.

Examples of scalp use cosmetic products include shampoos, rinse-in shampoos, and similar hair use cleansing agents; hair waxes, hair use curl holding agents, setting agents, hair creams, hairsprays, hair liquids, and similar hair dressing products; hair coloring substances, hair color sprays, hair color rinses, hair color sticks, and similar hair use coloration products; hair tonics, hair treatment essences, hair packs, and similar hair growing products; and oil rinses, cream rinses, treatment rinses, hair conditioners, hair treatments, and similar hair rinse or hair conditioning products. In addition, examples of bath use cosmetic products include bath foams.

The form of the cosmetic composition according to the present invention is not particularly limited, and these can be alternatively used in the form of a liquid, W/O emulsion, O/W emulsion, W/O cream-like, O/W cream-like, solid, paste-like, gel-like, powder-like, multi-layer, mousse-like, mist-like, granule, flake, crushed stone, and similar forms. Particularly preferable forms are W/O creams, solids, pastes, gels, and powders.

EXAMPLES

Hereinafter, the present invention is described in detail with reference to Practical Examples and Comparative Examples, but it should be understood that the present invention is not limited to these Practical Examples. The viscosity (kinetic viscosity) values are measured at 25° C.

Measurement of Platinum Metal Content

The value of platinum metal content in the silicone rubber powder was measured by Inductively Coupled Plasma Mass Spectrometry (ICP-MS; model: Agilent 7500a; manufactured by Yokogawa Analytical Systems, Inc.).

Measurement of Coloration

The degree of coloration of each of the silicone rubber powders was measured using a Color-guide 45°/0° colorimeter (manufactured by Gardner) using the measured b* (yellow color) value.

Reference Example 1

77.0 parts by mass of a dimethylvinylpolysiloxane represented by the average formula:

21.5 parts by mass of a dimethylmethylhydrogenpolysiloxane capped at both molecular terminals with trimethylsiloxy groups represented by the average formula:

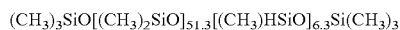

and an isopropyl alcohol solution of chloroplatinic acid (at an amount of 50 ppm in terms of mass units the content of the platinum metal of the present composition) were stirred uniformly at 5° C. to prepare an addition reaction curable silicone composition. Thereafter, this composition was dispersed in an aqueous solution at 25° C. that was composed of 50 parts by mass of purified water and 1.5 parts by mass of polyoxyethylene isocetyl ether. After this mixture was made further uniformly emulsified using a colloid mill, 50 parts by mass of purified water was added for dilution to prepare the emulsion.

Thereafter, this emulsion was heated and cured to prepare a uniform aqueous suspension of silicone rubber particles. Thereafter, the suspension was dried in a hot air circulating oven at 150° C. to prepare the silicone rubber powder. Particles of this silicone rubber powder were spherical. The average particle diameter was 6.2 µm, and the JIS A hardness was 60. Moreover, the coloration of the silicone rubber powder was −0.28 (b*), and the platinum metal (Pt) content was 7.2 ppm by mass.

Practical Example 1

300 parts by mass of water, 1.5 parts by mass of SANNONIC SS-120 (polyoxyethylene alkyl ether, HLB 14.5, produced by Sanyo Chemical Industries, Inc.), and 1.5 parts by mass of SANNONIC SS-30 (polyoxyethylene alkyl ether, HLB 8.0, produced by Sanyo Chemical Industries, Inc.) were added to 100 parts by mass of the silicone rubber powder obtained in Reference Example 1. This mixture was stirred and heated to 98° C. for 1 hour, and then was filtered. Then, 170 parts by mass of water was added to the residue, and the mixture was filtered again. The residue was then dried overnight in an oven at 40° C. to obtain silicone rubber powder. The coloration of the obtained silicone rubber powder was −0.82 (b*), and the platinum metal (Pt) content was 2.5 ppm by mass.

Practical Example 2

A silicone rubber powder was obtained in the same manner as in Practical Example 1, except for addition of 3 parts by mass of NIKKOL OT P-75 (sodium di(2-ethylhexyl) sulfosuccinate liquid; manufactured by Nikko Chemicals Co., Ltd.) rather than the SANNONIC SS-120 and SANNONIC SS-30. The coloration of the obtained silicone rubber powder was −0.74 (b*), and the platinum metal (Pt) content was 2.5 ppm by mass.

Practical Example 3

300 parts by mass of water, 1.5 parts by mass of SANNONIC SS-120 (polyoxyethylene alkyl ether, HLB 14.5, produced by Sanyo Chemical Industries, Inc.), and 1.5 parts by mass of SANNONIC SS-30 (polyoxyethylene alkyl ether, HLB 8.0, produced by Sanyo Chemical Industries, Inc.) were added to 100 parts by mass of the silicone rubber powder obtained in Reference Example 1. This mixture was stirred and heated to 50° C. for 1 hour, and then was filtered. Then, 170 parts by mass of water was added to the residue, and the mixture was filtered again. The residue was then dried overnight in an oven at 40° C. to obtain silicone rubber powder. The coloration of the obtained silicone rubber powder was −0.89 (b*), and the platinum metal (Pt) content was 1.8 ppm by mass.

Comparative Example 1

300 parts by mass of water was added to 100 parts by mass of the silicone rubber powder obtained in Reference Example 1. This mixture was stirred and heated to 98° C. for 4 hours, and then was filtered. The residue was then dried overnight in an oven at 40° C. to obtain silicone rubber powder. The coloration of the obtained silicone rubber powder was −0.28 (b*), and the platinum metal (Pt) content was 7.2 ppm by mass.

Comparative Example 2

200 parts by mass of toluene and 100 parts by weight of IPA were added to 100 parts by mass of the silicone rubber powder obtained in Reference Example 1, and the mixture was stirred for 1 hour. Then, after the mixture was allowed to stand overnight, the mixture was filtered. Then, 20 parts by mass of toluene was added to the residue, and the mixture was filtered again. The residue was then dried overnight in an oven at 40° C. to obtain silicone rubber powder. The coloration of the obtained silicone rubber powder was −0.69 (b*), and the platinum metal (Pt) content was 3.6 ppm by mass. Moreover, the obtained silicone rubber powder had an odor of toluene and IPA.

Reference Examples 2 and 3

The platinum metal contents of commercially obtainable silicone rubber powders were 8.1 ppm by mass (commercial product A1) and 6.7 ppm by mass (commercial product A2).

The results and platinum metal contents in the silicone rubber powders are shown below in Table 1. When treatment was performed using aqueous solution (50° C. or 99° C.) including surfactant, there was a difference versus the comparative examples and commercial products in that the platinum metal content was reduced to a level ≤3.5 ppm by mass, and it was confirmed that such reduction was useful in that there was no occurrence of the problems of odorization and discoloration.

Table 1: Platinum Metal Content in Silicone Rubber Powders Obtained by Each Processing

TABLE 1

|  | Practical Examples | | | Comparative Examples | |
| --- | --- | --- | --- | --- | --- |
|  | 1 | 2 | 3 | 1 | 2 |
| Processing | nonionic type surfactant aqueous solution/ temperature: 98° C. | anionic type surfactant aqueous solution/ temperature: 98° C. | nonionic type surfactant aqueous solution/ temperature: 50° C. | water alone/ temperature: 98° C. | Toluene/IPA |
| Platinum metal content (ppm by mass) | 2.5 | 2.5 | 1.8 | 7.2 | 3.6 |

|  | Reference Examples | | |
| --- | --- | --- | --- |
|  | 1 | 2 | 3 |
| Processing | non-treated product | commercial product A1 | commercial product A2 |
| Platinum metal content (ppm by mass) | 7.2 | 8.1 | 6.7 |

The invention claimed is:

1. A hydrosilylation reaction-crosslinked silicone rubber powder having a platinum metal content ≤3.5 ppm by mass.

2. The hydrosilylation reaction-crosslinked silicone rubber powder as claimed in claim 1, wherein the platinum metal content is in a range of 1.5 to 3.0 ppm by mass.

3. The hydrosilylation reaction-crosslinked silicone rubber powder as claimed in claim 1, wherein the average particle diameter of the silicone rubber powder is from 0.1 μm to 10 mm.

4. The hydrosilylation reaction-crosslinked silicone rubber powder as claimed in claim 1, obtained by washing a silicone rubber powder containing at least 5 ppm by mass of platinum metal using an aqueous solution heated to a temperature of 30° C. to 99° C. and containing at least one type of surfactant.

5. A method of producing a hydrosilylation reaction-crosslinked silicone rubber powder, the method comprising:
    washing a silicone rubber powder containing at least 5 ppm by mass of platinum metal using an aqueous solution of at least one type of surfactant to lower platinum content in the silicone rubber powder;
    wherein the hydrosilylation reaction-crosslinked silicone rubber powder produced has a platinum metal content ≤3.5 ppm by mass.

6. The method as claimed in claim 5, wherein the surfactant is selected from the group consisting of anionic surfactants, cationic surfactants, nonionic surfactants, and amphoteric surfactants.

7. The method as claimed in claim 5, wherein the aqueous solution of at least one type of surfactant is heated to a temperature of 30° C. to 99° C.

8. The method as claimed in claim 5, wherein the concentration of surfactant in the aqueous solution is in the range of 0.1 to 10% by mass.

9. The method as claimed in claim 5, wherein the surfactant is a nonionic surfactant.

10. The method as claimed in claim 9, wherein the surfactant is selected from a polyoxyethylene alkyl ether or a sodium diethylhexyl sulfosuccinate.

11. A method of producing a hydrosilylation reaction-crosslinked silicone rubber powder, the method comprising
    (a) producing a silicone rubber powder by curing a composition comprising:
        (A) an organopolysiloxane having at least two alkenyl groups in a molecule;
        (B) an organohydrogenpolysiloxane having at least two silicon-bonded hydrogen atoms in a molecule; and
        at least 5.0 ppm by mass of a platinum-based catalyst, in terms of a platinum metal content, relative to the mass of a cured product resulting from crosslinking component (A) and component (B); and (b) washing at least once the silicone rubber powder using at least 50 parts by mass of an aqueous solution heated to a temperature of 30° C. to 99° C. containing at least 0.1% by mass of at least one type of surfactant, per 100 parts by mass of the silicone rubber powder, to obtain a silicone rubber powder having a platinum metal content ≤3.5 ppm by mass.

12. A cosmetic composition comprising:
(i) hydrosilylation reaction-crosslinked silicone rubber powder as claimed in claim 1; and
(ii) at least one cosmetic raw material.

13. The hydrosilylation reaction-crosslinked silicone rubber powder as claimed in claim 2, wherein the average particle diameter of the powder is from 0.1 μm to 10 mm.

14. The hydrosilylation reaction-crosslinked silicone rubber powder as claimed in claim 13, obtained by washing a silicone rubber powder containing at least 5 ppm by mass of platinum metal using an aqueous solution heated to a temperature of 30° C. to 99° C. containing at least one type of surfactant.

15. The method as claimed in claim 5, wherein the platinum metal content is in a range of 1.5 to 3.0 ppm by mass.

16. The method as claimed in claim 6, wherein the aqueous solution of at least one type of surfactant is heated to a temperature of 30° C. to 99° C.

17. The method as claimed in claim 16, wherein the concentration of surfactant in the aqueous solution is in the range of 0.1 to 10% by mass.

18. The method as claimed in claim 11, wherein the platinum metal content is in a range of 1.5 to 3.0 ppm by mass.

19. The method as claimed in claim 11, wherein the concentration of surfactant in the aqueous solution is in the range of 0.1 to 10% by mass.

20. The method as claimed in claim 19, wherein the surfactant is a nonionic surfactant, alternatively is selected from a polyoxyethylene alkyl ether or a sodium diethylhexyl sulfosuccinate.

* * * * *